(12) United States Patent
Gattani et al.

(10) Patent No.: US 7,794,396 B2
(45) Date of Patent: Sep. 14, 2010

(54) SYSTEM AND METHOD FOR THE AUTOMATED ZOOMING OF A SURGICAL CAMERA

(75) Inventors: Abhishek Gattani, San Jose, CA (US); Salmaan Hameed, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 985 days.

(21) Appl. No.: 11/592,671

(22) Filed: Nov. 3, 2006

(65) Prior Publication Data

US 2008/0108873 A1 May 8, 2008

(51) Int. Cl.
*A61B 1/04* (2006.01)
*A61B 1/00* (2006.01)

(52) U.S. Cl. .................. 600/173; 600/118; 600/168; 348/65

(58) Field of Classification Search .............. 600/109, 600/112, 117, 118, 160, 167, 168, 173; 348/65
See application file for complete search history.

(56) References Cited

U.S. PATENT DOCUMENTS

| | | | | |
|---|---|---|---|---|
| 5,582,576 A | * | 12/1996 | Hori et al. | 600/167 |
| 5,836,869 A | * | 11/1998 | Kudo et al. | 600/173 |
| 5,839,000 A | * | 11/1998 | Davis et al. | 396/51 |
| 6,919,914 B2 | * | 7/2005 | Beutter et al. | 348/65 |
| 6,930,705 B2 | * | 8/2005 | Tanaka | 348/45 |
| 7,564,994 B1 | * | 7/2009 | Steinberg et al. | 382/118 |
| 2005/0267335 A1 | * | 12/2005 | Okada et al. | 600/173 |
| 2008/0231692 A1 | * | 9/2008 | Higuchi et al. | 348/65 |
| 2009/0015658 A1 | * | 1/2009 | Enstad et al. | 348/14.08 |
| 2009/0220131 A1 | * | 9/2009 | Cinquin et al. | 382/128 |

OTHER PUBLICATIONS

System and Method for 3-D Tracking of Surgical Instrument in Relation to Patient Body, U.S. Appl. No. 11/388,756, filed Mar. 24, 2006, Abhishek Gattani et al.

* cited by examiner

*Primary Examiner*—John P Leubecker
*Assistant Examiner*—Jeffrey H Chang
(74) *Attorney, Agent, or Firm*—Flynn, Thiel, Boutell & Tanis, P.C.

(57) ABSTRACT

A system and method for automatically reconfiguring the magnification or zoom level of a surgical camera based upon the detection of a surgical instrument or defined anatomical feature. Utilizing image analysis algorithms, the video images generated by the surgical camera are analyzed for the presence of defined patterns, colors, motion and the like, representing a defined surgical instrument or anatomical feature. Upon detection of a surgical instrument or anatomical feature, the system can automatically adjust the actual or effective focal range of the surgical camera, and thus change the magnification or zoom level of the camera, based on the type of surgical instrument or anatomical feature detected.

20 Claims, 10 Drawing Sheets

SYSTEM AND METHOD FOR THE AUTOMATED ZOOMING OF A SURGICAL CAMERA

FIELD OF THE INVENTION

The present invention relates to a system and method for adjusting the magnification of a surgical camera and, more specifically, to a system and method for automatically adjusting the magnification or zoom level of a surgical camera depending on a detected presence or state of a surgical instrument or anatomical feature.

BACKGROUND OF THE INVENTION

A primary goal of minimally invasive surgical procedures is to minimize the adverse effects of the procedure on the patient. This reduces post-surgical trauma and pain and minimizes recovery time. Some minimally invasive procedures require the surgeon to create one or more small incisions through which various surgical cameras must be passed, thereby allowing the surgeon to visualize the tissue of the patient under investigation.

These surgical cameras typically have the capability to magnify or zoom in upon the tissue being observed, thereby allowing for a larger image of the tissue having greater detail. However, traditional surgical cameras usually require the surgeon or his or her assistant to manually adjust the zoom or magnification level of the camera whenever the surgeon desires to see the tissue in less or greater detail. As a result, these traditional surgical camera systems are more difficult to operate than necessary, and require the surgeon to direct his attention away from his or her examination of the tissue whenever he or she needs to adjust the magnification level of the camera.

SUMMARY OF THE INVENTION

A system and method for automatically reconfiguring the magnification or zoom level of a surgical camera based upon the detection of a surgical instrument or defined anatomical feature. Utilizing image analysis algorithms, the video images generated by the surgical camera are analyzed for the presence of defined patterns, colors, motion and the like, representing a defined surgical instrument or anatomical feature. Upon detection of a surgical instrument or anatomical feature, the system can automatically adjust the actual or effective focal range of the surgical camera, and thus change the magnification or zoom level of the camera, based on the type of surgical instrument or anatomical feature detected.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which.

DETAILED DESCRIPTION

Auto-Zooming Camera System

Figure 1:
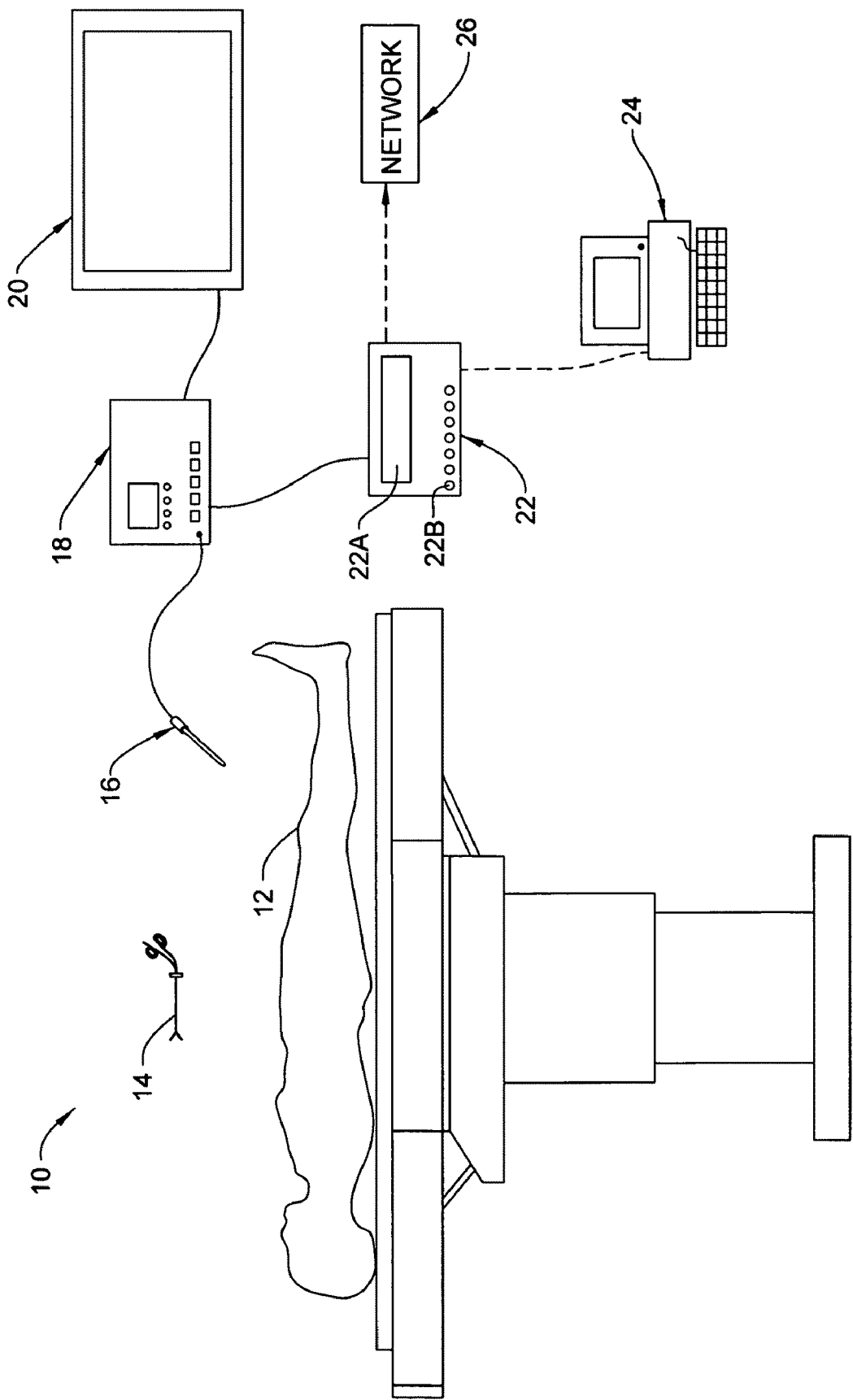
FIG. 1 illustrates an auto-zooming surgical camera system according to a first embodiment.

FIG. 1 depicts an auto-zooming surgical camera system 10 (hereafter referred to as "auto-zoom system") according to a first embodiment of the invention. Included in system 10 is a surgical camera 16, such as, for example, an endoscopic camera that allows a surgeon to view the internal tissue of a patient 12 and subsequently operate on the tissue with one or more surgical instruments 14 that are passed through small incisions in the patient 12 during a minimally invasive surgical procedure. (Surgical camera 16 will hereafter be referred to as an "endoscope 16".) Communicating with the endoscope 16, either via wired or wireless connection, is an endoscope control unit 18 that is configured to control the endoscope 16 and process the images captured by the endoscope 16 into a video signal. FIG. 1 depicts endoscope control unit 18 as being a separate component from the endoscope 16. However, according to some alternative embodiments, endoscope control unit 18 may be incorporated within the endoscope 16 itself. Connecting to the endoscope control unit 18 is a video monitor 20, such as a LCD video monitor, for receiving and displaying the video signal generated by the endoscope control unit 18.

Connecting to the endoscope control unit 18, either via wired or wireless connection, is a camera zoom control unit 22 (hereafter referred to as "zoom control unit 22"). As will be discussed in greater detail below, the zoom control unit 22 continuously applies one or more image recognition algorithms to the video signal generated by endoscope control unit 18. In response to a recognizable surgical instrument or anatomical feature being detected, the zoom control unit 22 will automatically adjust the "zoom" of the camera by adjusting the actual and/or effective focal length of the endoscope 16, thereby enlarging or reducing the image being generated by the endoscope 16.

The zoom control unit 22 can include one or more displays 22A as well as a plurality of switches 22B, such as buttons and/or a keypad, for programming the zoom control unit 22. According to another embodiment, the zoom control unit 22 may also connect to a separate computer 24 that can be used to program the zoom control unit 22.

A plurality of image analysis algorithms, which are used in the detection of surgical instruments and anatomical features within the endoscopic image, are stored within a memory of the zoom control unit 22. However, according to another embodiment, the image analysis algorithms can be stored in a remote database that is maintained in computer 24, or alternatively, stored in a remote database that is maintained within a network 26 that is in communication with zoom control unit 22.

General Operation of the Auto-Zooming Camera System

Figure 2:
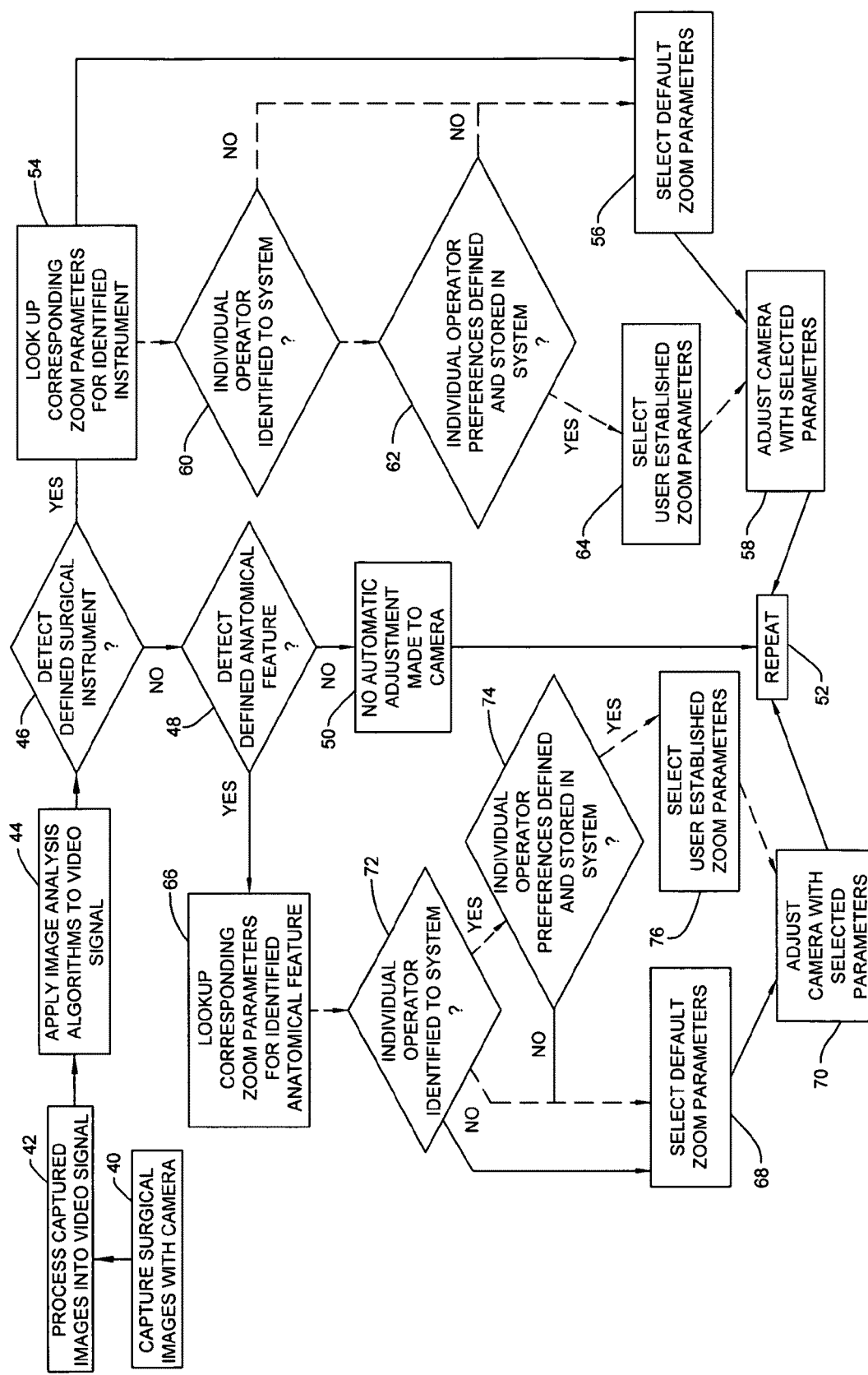
FIG. 2 illustrates the general operation of an auto-zooming surgical camera system according to one embodiment.

General operation of the auto-zoom system 10 according to one embodiment will now be described with reference to the flow chart of FIG. 2. Images of the surgical scene are first captured by the endoscope (step 40) and then processed into a video signal (step 42). The zoom control unit 22 then applies one or more predefined image analysis algorithms to the video signal (step 44). Through application of the image analysis algorithms, the zoom control unit 22 determines whether a recognizable surgical instrument 14 is present (step 46). If no recognizable surgical instrument is detected, the zoom control unit 22 proceeds to apply additional image analysis algorithms to determine whether any defined anatomical features are present in the endoscopic image (step 48). If no defined anatomical features are detected, then no automatic adjustments are made to the zoom level of the endoscopic camera 16 (step 50). The process then repeats (step 52).

If a surgical instrument 14 is detected in step 46, then the zoom control unit 22 proceeds to lookup the predetermined default zoom parameters associated with the detected surgical instrument (step 54). The default zoom parameters associated with the detected instrument are subsequently selected by the zoom control unit 22 (step 56), which then proceeds to adjust the zoom level of the endoscope 16 on the basis of the selected zoom parameters (step 58).

A similar process to that described above is applied if a defined anatomical feature is detected by the system in step 48. Specifically, the zoom control unit 22 proceeds to lookup the predefined zoom parameters corresponding to the identified anatomical feature (step 66), select those predefined zoom parameters (step 68), and then automatically adjust the zoom level of the endoscopic camera 16 on the basis of the selected zoom parameters (step 70).

According to one variation of the above-described embodiment, the auto zoom system 10 not only stores a set of default zoom parameters associated with a predefined surgical instrument or anatomical feature, but also permits a user (e.g., surgeon) to store and associate their own custom zoom parameters. Thus, the default zoom parameters may call for the endoscope 16 to be automatically adjusted to a 2× zoom level upon detection of a specific surgical instrument 14, while a surgeon's custom zoom parameters may call for the endoscope 16 to be automatically adjusted to a 3× zoom level upon detection of the same surgical instrument 14. According to this alternative embodiment, the specific surgeon utilizing the system 10 is initially identified to the system 10 by means of, for example, the entry of a user identification code at the beginning of the surgical procedure.

Accordingly, when the system 10 detects a surgical instrument (step 46) and initiates the lookup of the corresponding zoom parameters (step 54), the system first determines whether the individual operating the system (e.g., surgeon) has been identified to the system 10 (step 60). If so, the system 10 proceeds to determine whether the identified person has defined and stored any zoom parameters within the system 10 (step 62), and if so, selects the user-established zoom parameters associated with the detected instrument 14 (step 64) and then automatically adjusts the endoscope 16 accordingly. A similar process occurs upon detection of a defined anatomical feature (see steps 72-76).

In the embodiment described above with respect to FIG. 2, the system 10 is configured to first attempt to detect a predefined surgical instrument 14 and subsequently implement a set of zoom parameters upon the endoscope 16 if an instrument is detected. If no instrument is detected, then the system scans the image, attempts to detect any predefined anatomical features, and subsequently implement a corresponding set of zoom parameters if such an anatomical feature is detected. According to one alternative embodiment, auto-zoom system 10 is configured to first analyze an endoscopic image to detect a predefined anatomical feature, and subsequently implement a set of corresponding zoom parameters if such an anatomical feature is detected. If no such feature is detected, then the system analyzes the image in order to detect the presence of any predefined surgical instruments 14 and implement a corresponding set of zoom parameters.

In the above two embodiments, auto-zoom system 10 implements a set of zoom parameters in response to either the detection of a surgical instrument 14 or the detection of an anatomical feature. However, according to a third embodiment, system 10 is also capable of automatically zooming an endoscope 16 on the basis of a set of zoom parameters in response to detecting a predefined surgical instrument 14 in combination with a predefined anatomical feature. Accordingly, an endoscope 16 can be automatically zoomed to a first level upon detection of a surgical instrument 14, zoomed to a second level upon detection of an anatomical feature, and automatically zoomed to a third level upon detection of both a surgical instrument 14 and an anatomical feature.

Automatic Tracking of Detected Instrument/Anatomical Feature

In one embodiment of the invention, the auto-zoom system 10 is configured to automatically control the zoom level of an endoscopic camera 16 so as to try and maintain a detected surgical instrument 14 or anatomical feature within the field of view of the endoscope. According to this embodiment, the zoom parameters associated with a detected instrument or anatomical feature will attempt to maintain a specified zoom level as long as the detected instrument or feature is generally maintained within the center of the endoscopic camera's field of view. However, if either the endoscope 16 or instrument 14 is repositioned, the detected instrument 14 or anatomical feature may no longer be within the field of view of the endoscope, and thus no longer visible. In order to prevent a detected instrument 14 or anatomical feature from being removed from the endoscopic camera's field of view, the auto-zoom system 10 automatically reduces the zoom level of the endoscope. As a result, the field of view of the endoscopic camera increases, and the previously detected instrument 14 or anatomical feature becomes visible once again.

Figure 3A:
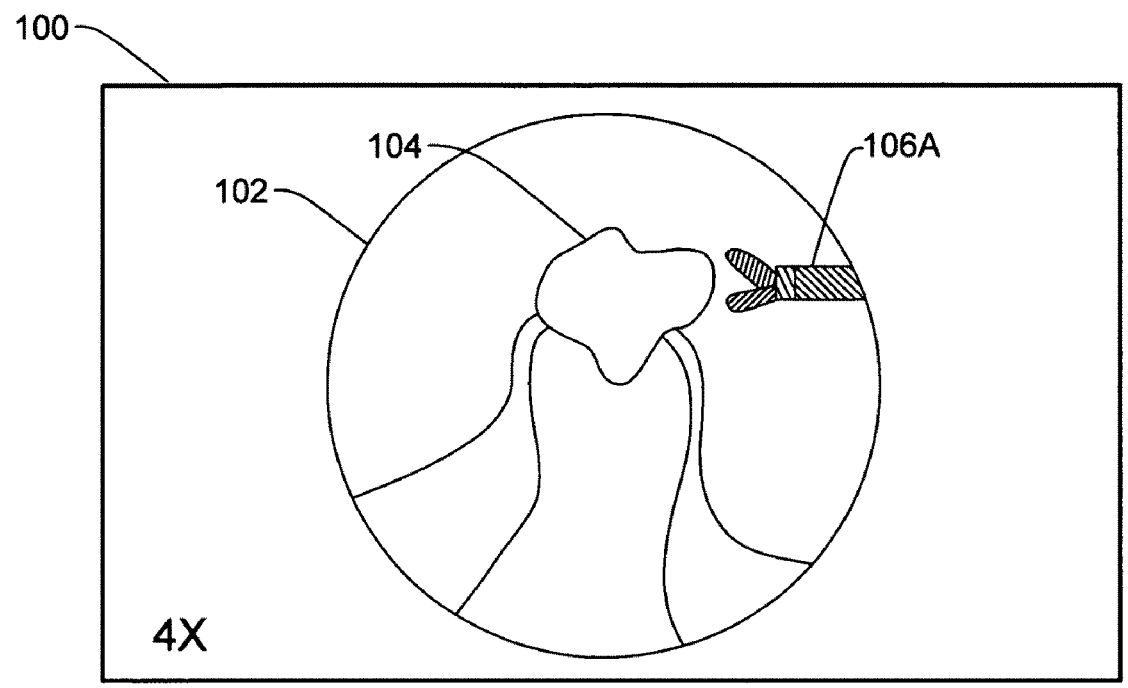
FIGS. 3A-3C illustrate the automatic zooming of a surgical camera in order to maintain a detected surgical instrument within the field of view of the surgical camera.
Figure 3B:
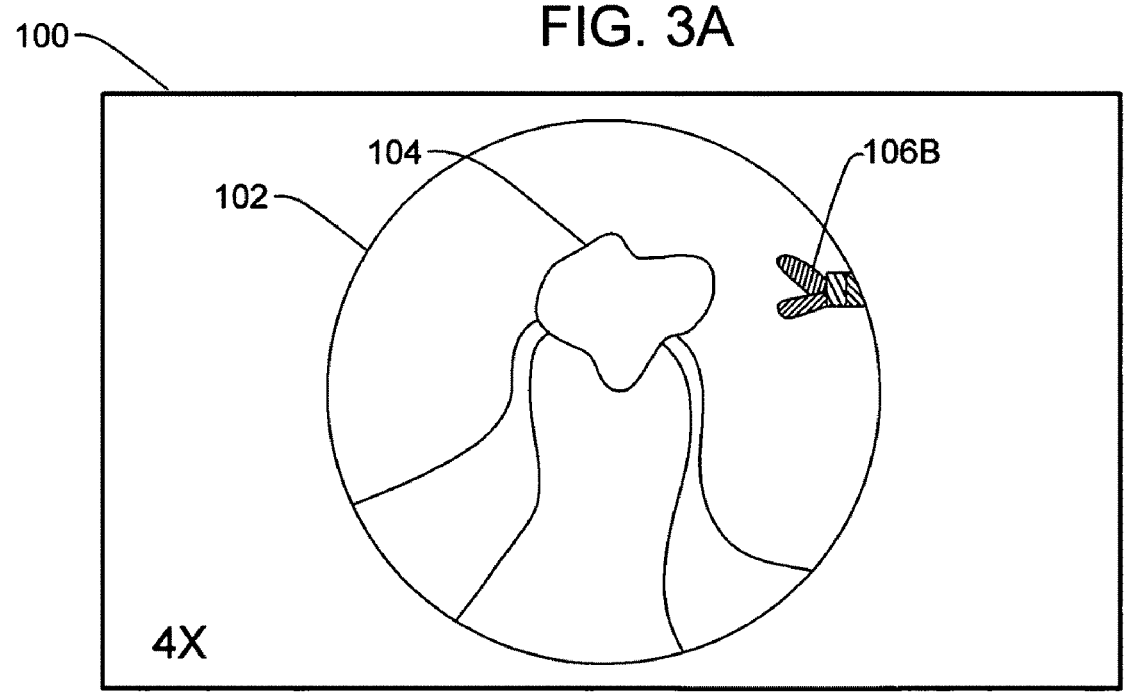
Figure 3C:
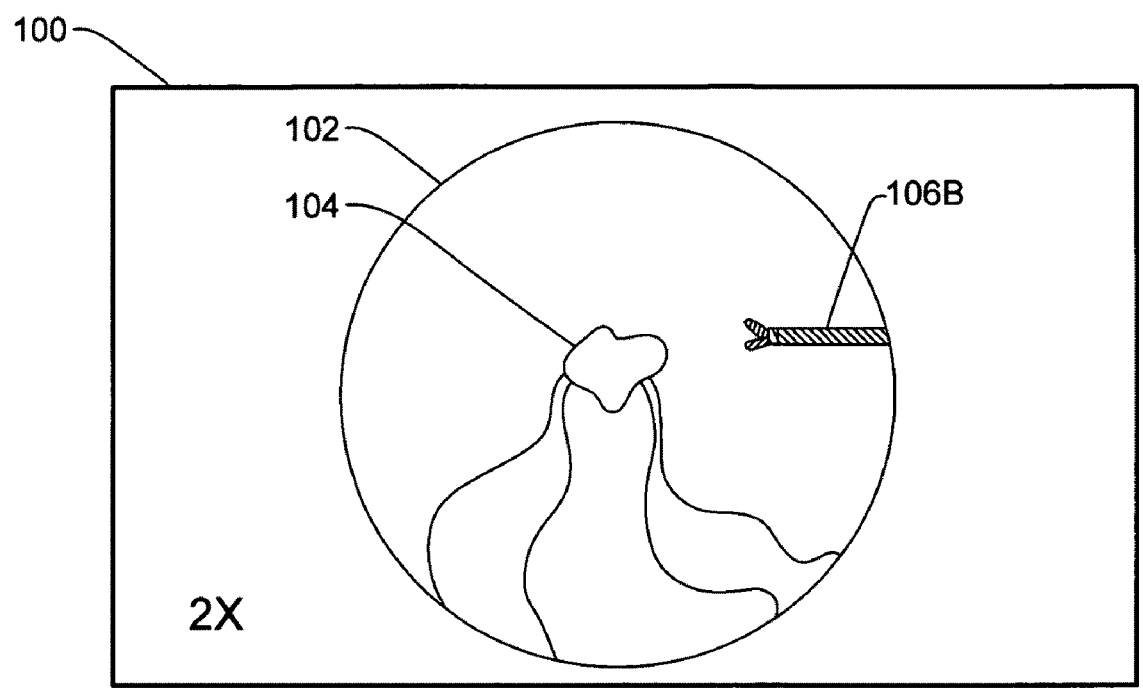

As an example of the above embodiment, see FIGS. 3A-3C, which depict a video monitor 100 upon which is displayed an endoscopic image 102 representing the field of view of an endoscope 16 that is initially maintained at a 4× zoom level. As illustrated in FIG. 3A, a certain anatomical feature 104 is located roughly within the center of the image 102. Similarly, a detected instrument 106A is currently positioned relatively near the anatomical feature 104. As illustrated in FIG. 3B, the surgeon subsequently relocates the surgical instrument to a second location 106B that is farther away from the anatomical feature 104 and in danger of being completely removed from the endoscopic camera's current field of view. To prevent the surgical instrument from being completely removed from the endoscopic image 102, the auto-zoom system 10 attempts to "track" the instrument 106B by reducing the zoom level of the endoscope, thereby increasing the field of view or area that the endoscope 16 can visualize. Thus, as illustrated in FIG. 3C, the auto-zoom system 10 automatically reduces the zoom of the endoscope 16 from a 4× zoom level to a 2× zoom level, thereby increasing the field of view of the endoscope 16 and bringing more of the instrument 106B into view.

Automatic Magnification of Tissue Region Corresponding to Detected Instrument/Anatomical Feature According to another embodiment, the auto-zoom system 10 is configured to automatically control the zoom level of an endoscopic camera 16 so as to maximize the amount of detail of a tissue area being observed through the endoscope 16. This is accomplished by programming the system 10 with zoom parameters that, upon detection of a predefined surgical instrument 14 or anatomical feature, direct the endoscope 16 to automatically increase its zoom level (e.g., zoom from 2× to 4×). In this manner, a surgeon can be endoscopically examining an area of tissue at a 2× zoom level to generally determine, for example, the best area to locate a series of surgical staples within the tissue. Once the general area has been selected, the surgeon directs the stapler to the surgical scene. The stapler and surrounding tissue area subsequently becomes imaged by the endoscope 16. Image analysis algorithms applied by zoom control unit 22 subsequently detect the presence of the stapler and apply a series of zoom parameters that cause the endoscope to zoom in and provide greater detail of the tissue surrounding the area where the staples are to be applied.

Figure 4A:
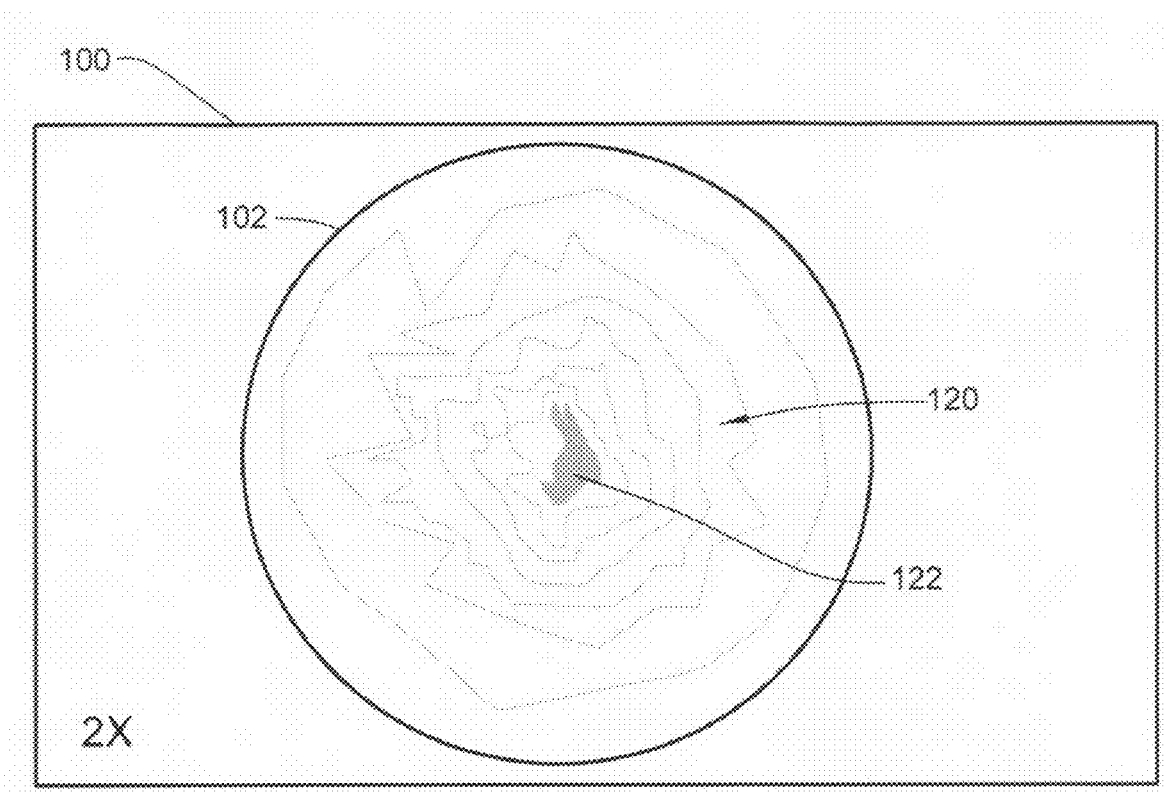
FIGS. 4A-4B are an illustrative example of the automatic zooming of a surgical camera in response to detecting an anatomical feature of interest.
Figure 4B:
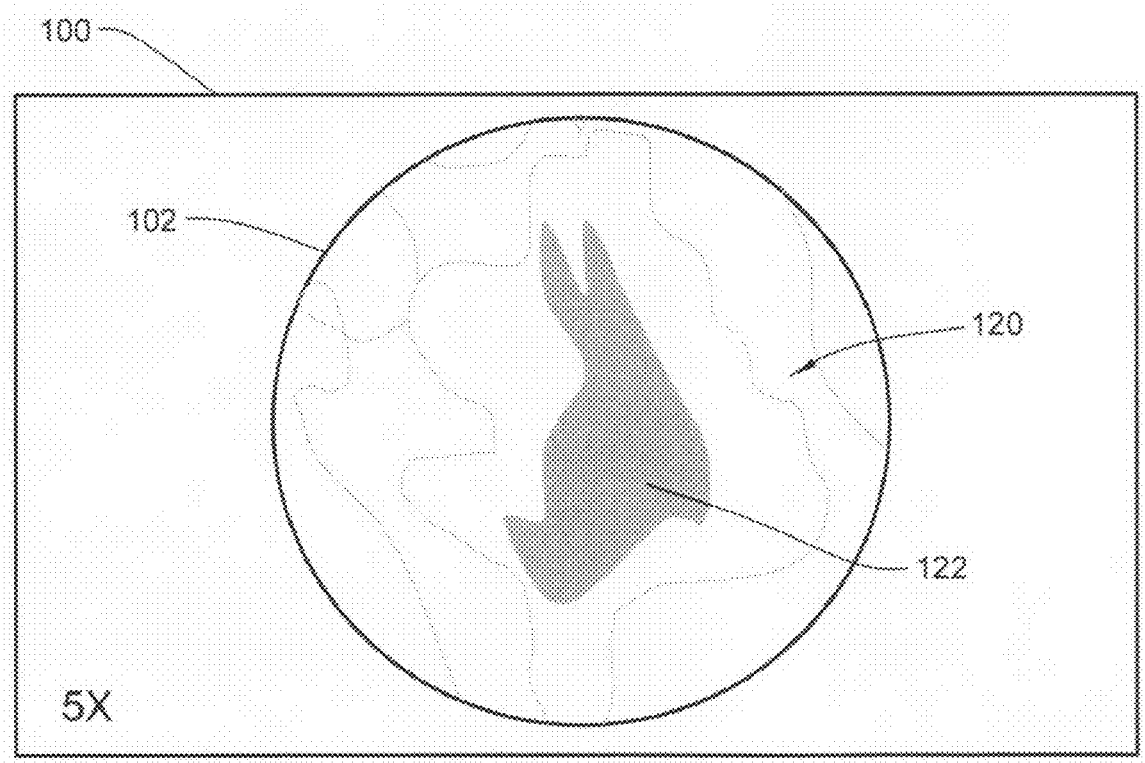

Consider a first example where the auto-zoom system 10 is configured to automatically zoom in on any detected tissue lesions so as to provide the examining surgeon the best detail possible for diagnostic purposes. FIGS. 4A and 4B illustrate a video monitor 100 upon which is displayed an endoscopic image 102 representing the field of view of an endoscope 16 currently being utilized to examine some tissue 120. As depicted in FIG. 4A, through the application of one or more image analysis algorithms upon the endoscopic image, the zoom control unit 22 detects a previously defined type of tissue lesion 122 while an area of tissue is being examined at a 2× zoom level. As then illustrated in FIG. 4B, the zoom parameters associated with this specific anatomical feature direct the endoscope 16 to automatically increase its zoom level to 5× so as to provide a close-up image of the lesion 122. Accordingly, without any intervention, the examining surgeon is automatically presented with a magnified image of the lesion 122 upon detection of the lesion 122 by auto-zoom system 10.

Optical Verses Digital Zoom

It should be noted in the above example that during examination and subsequent detection, the endoscope 16 was positioned in such a manner that the anatomical feature in question (lesion 122) was generally located within the center of the endoscopic image 102. Accordingly, an optical-based "zooming" of the endoscopic camera, where the actual focal length of the camera is adjusted through displacement of the camera's lens system, is effective in providing a more detailed image of the lesion 122.

Figure 5A:
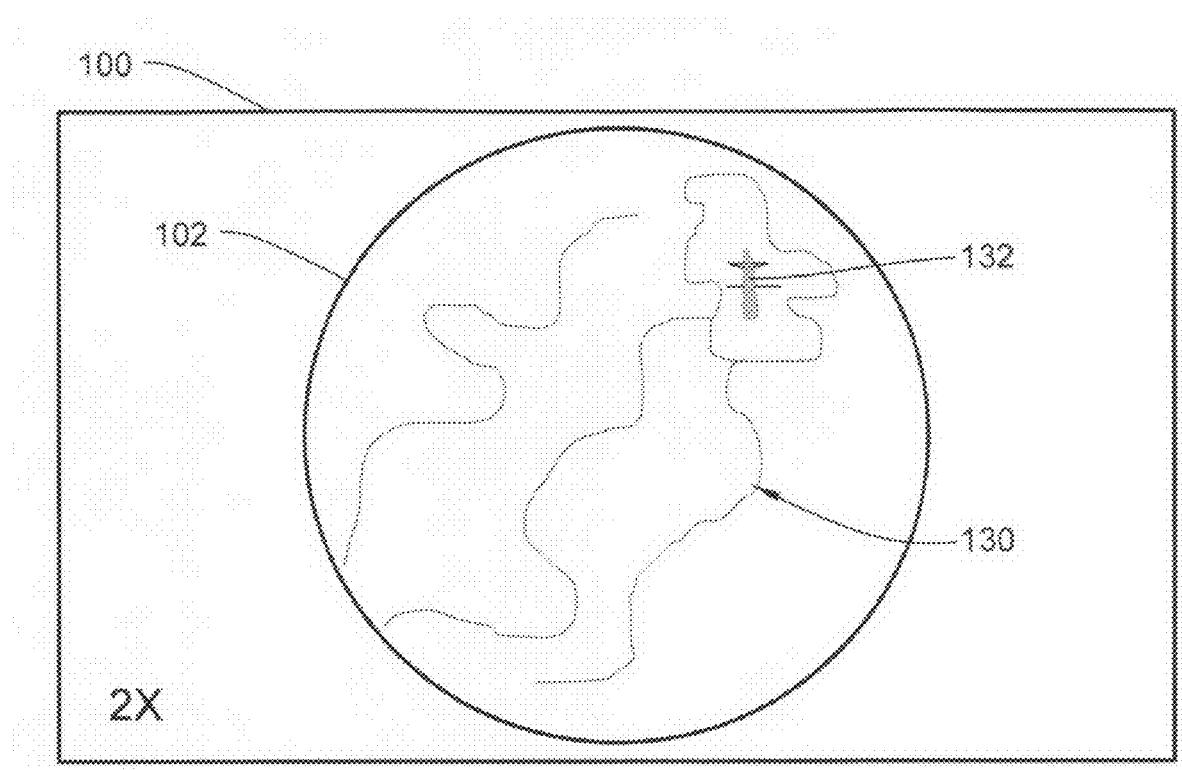
FIGS. 5A-5B are an illustrative example of the automatic digital zooming of a surgical camera in response to detecting an anatomical feature of interest.
Figure 5B:
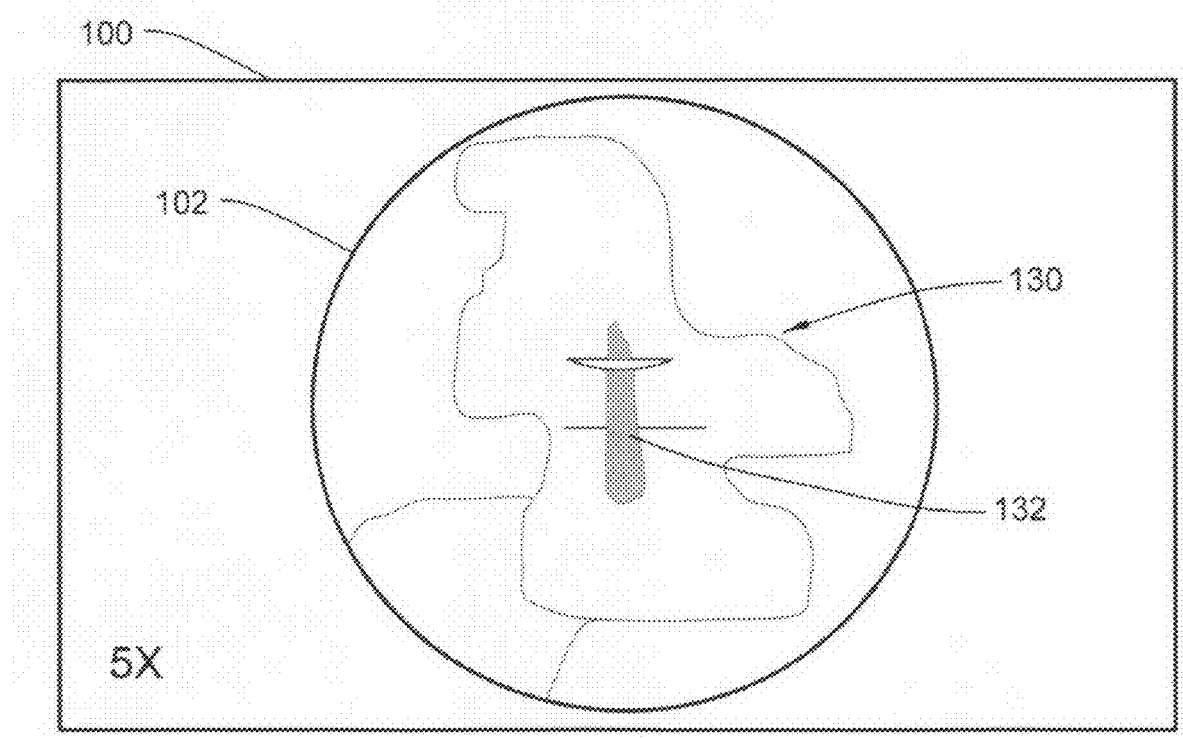

FIGS. 5A and 5B illustrate a similar example to that depicted in FIGS. 4A and 4B. Specifically, FIG. 5A depicts an endoscopic image 102 of an area of tissue 130 containing a unique anatomical feature 132. However, unlike the example of FIG. 4A, the unique anatomical feature 132 in question is not centered within the endoscopes field of view, but instead is located near the edge or boundary of the image 102. As a result, any automatic zooming of the image using an optical zoom would likely result in an image that no longer contains the anatomical feature 132 being examined. This is because as the endoscopic camera is optically zoomed, the center area of the initial image becomes enlarged while the periphery of the initial image is cut-off or removed from the zoomed image. Consequently, for the example depicted in FIGS. 5A and 5B, the auto-zoom system would have to rely on an endoscope's digital zooming capability where digital image interpolation allows for any region of the initial image, including peripheral regions, to be isolated and expanded. Thus, as depicted in FIG. 5B, the system 10 can detect anatomical feature 132 and subsequently direct the endoscope to isolate and digitally zoom in on the anatomical feature 132.

Multiple Views of Endoscopic Region

Figure 6:
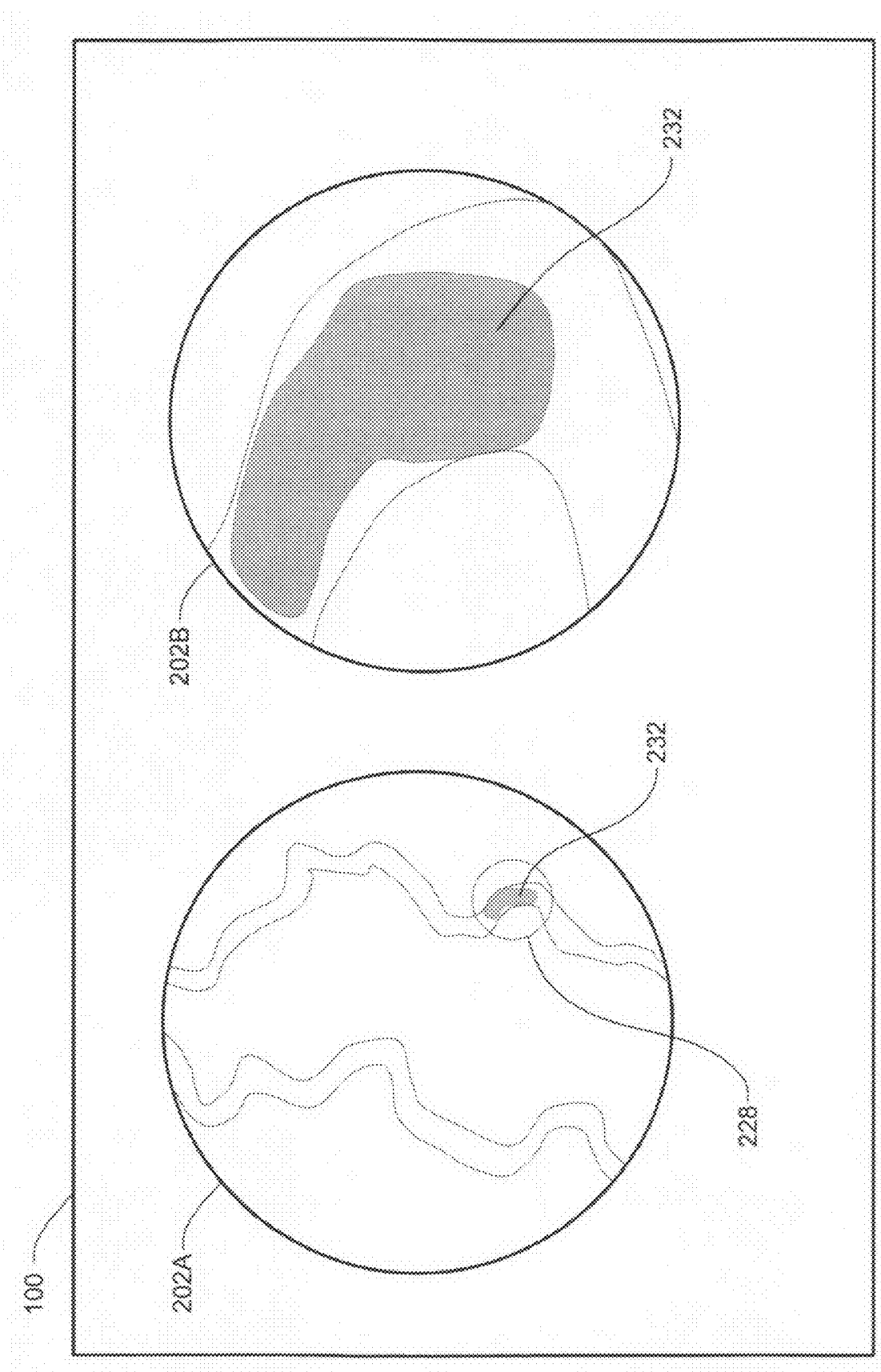
FIG. 6 illustrates an embodiment where the same surgical camera image is depicted by two different views having different degrees of magnification or zoom.

According to another embodiment, auto-zoom system 10 can be configured to display two different views of an endoscopic image at the same time. This can be accomplished in numerous ways, including, for example, but not limited to, the use of dual monitors, the dividing of a single monitor into regions so as to be capable of displaying dual pictures, the utilization of picture-in-picture techniques, or the use of a separate wearable or heads-up display. FIG. 6 depicts one example where a single monitor 100 displays side-by-side dual endoscopic images 202A and 202B. Image 202A depicts a typical endoscopic image of an area of tissue containing an anatomical feature of interest 232. Through application of one or more image analysis algorithms, zoom control unit 22 detects the anatomical feature 232 and automatically initiates magnification of the feature 232 by means of digital zoom technology. However, unlike the example of FIG. 5, the digitally-zoomed region of tissue 202B is not displayed in place of the original endoscopic image 202A, but instead is displayed next to the original endoscopic image. In this manner, the surgeon can simultaneously view the original endoscopic image depicted at a first scale, and also view the sub-region of interest depicted at a second, magnified scale.

A further variation of the above embodiment includes the auto-zoom system 10 superimposing some form of graphical object on the original, non-zoomed endoscopic view 202A, such as, for example, a ring 228 as illustrated in FIG. 6, that indicates the area of tissue being displayed in the digitally-zoomed view 202B. The superimposing of such a graphical object on the original endoscopic view 202A can also be utilized as a guidance aid for the surgeon, allowing the endoscope to be easily repositioned so that the anatomical feature 232 under examination is located at the center of the endoscope's field of view.

Automatic Switching Between Digital and Optical Zoom

In the embodiments above, optical zooming techniques were utilized to magnify a region of tissue generally located within the center of the endoscopic image, while digital zooming techniques were utilized to magnify a region of tissue generally located more on the periphery of an endoscopic image. According to a further embodiment, auto-zoom system 10 can be configured to implement the automatic switching between digital zoom and optical zoom when a tissue region under investigation becomes centered within the endoscope's field of view. Specifically, a region of tissue in the periphery of an endoscope's field of view can initially be magnified by digital zooming techniques. The surgeon can then reposition the endoscope so as to locate the region under investigation within the center of the endoscope's field of view. The system 10 subsequently determines that the tissue region being examined, which is associated with the detected instrument or anatomical feature, is now centered within the endoscope's field of view and will automatically regenerate the magnified view of that region using optical zoom techniques instead of digital zoom techniques that generally produce inferior quality images.

Image Analysis Algorithms and Surgical Instrument Markings

As previously discussed, auto-zoom system 10 utilizes one or more image analysis algorithms to detect specific features of an endoscopic image, including the presence of specific surgical tools as well as certain defined anatomical features. These algorithms generally analyze the video image for specific shapes, colors, patterns and light/chromatic intensities to detect specific anatomical features, such as blood vessels, lesions and the like. The sensing of motion can also be utilized to detect blood perfusion, aiding in the identification of blood vessels as well as bleeding. Similar detections means are used to identify the presence of specific surgical tools, evaluating, among other things, the shape, size and color of the tool.

Figure 7:
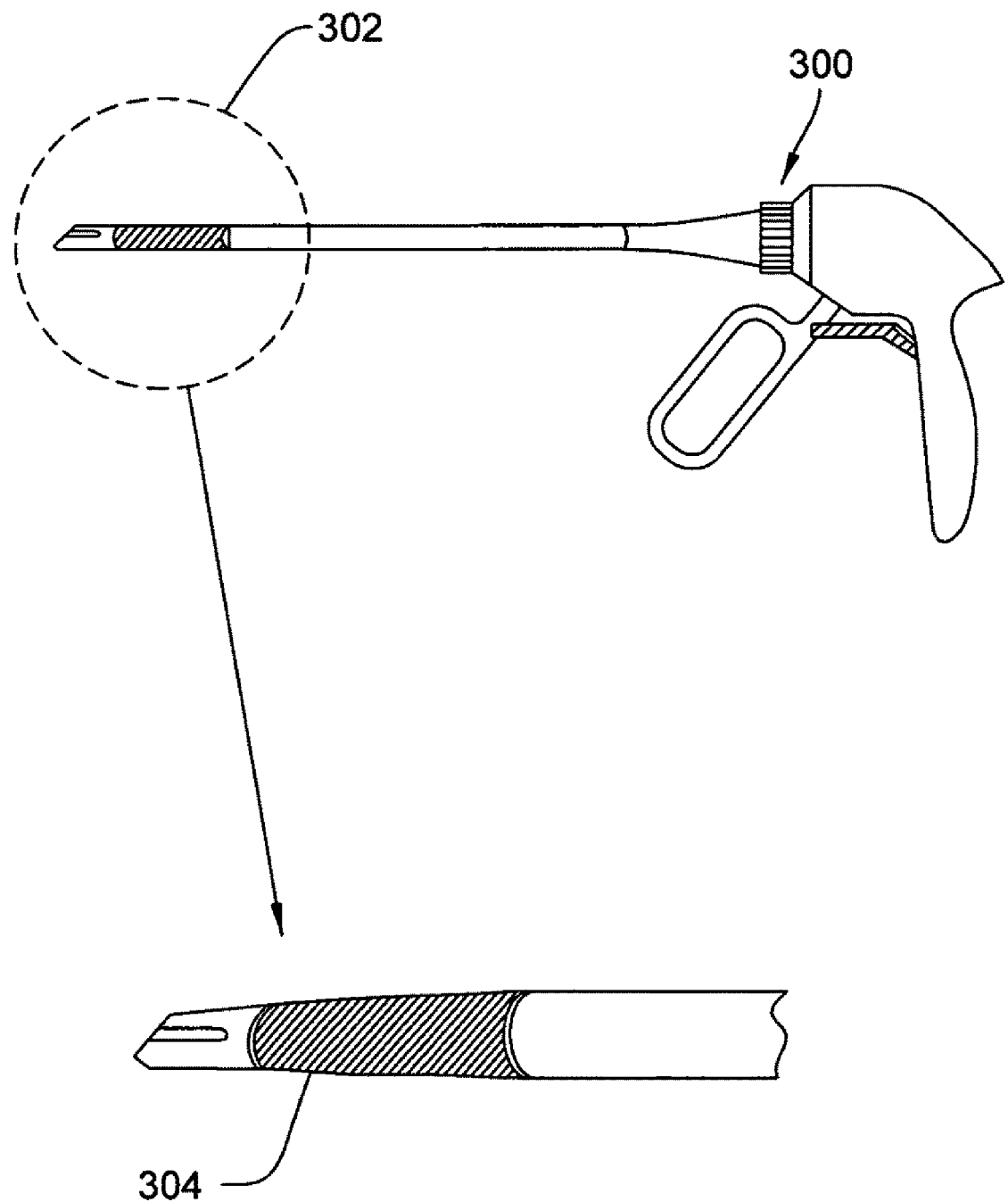
FIG. 7 depicts a surgical instrument having a distinct region designed to be readily detected by the system.

According to an additional embodiment, image analysis and detection of surgical instruments can be further assisted by providing unique markings on the instruments that more readily appear in the endoscopic image and are easier to detect through image analysis. Consider the example of FIG. 7, which depicts a surgical stapler 300 for endoscopic surgeries. To improve the detection of the instrument by image analysis, the distal end 302 of the stapler 300 includes a region 304 marked by a distinct pattern and/or color(s) that are more readily distinguished from the remainder of the instrument 300 as well as the surrounding tissue. The image analysis algorithms designed to detect surgical instruments can then be configured to further assess the endoscopic image for the distinct markings contained on the instruments. Then, as previously discussed, upon detection of an instrument, the system 10 can automatically control the magnification or zoom of the camera in order to provide a more detailed view of an area, or alternatively, try to keep an instrument or anatomical feature within the field of view of the camera.

In one embodiment of the invention, a surgical instrument can include two separate and unique markings, both of which should be detectable by the auto-zoom system 10 and allow detection of the instrument in general, as well as distinguishing one region of the surgical instrument from another region of the instrument.

Figure 8:
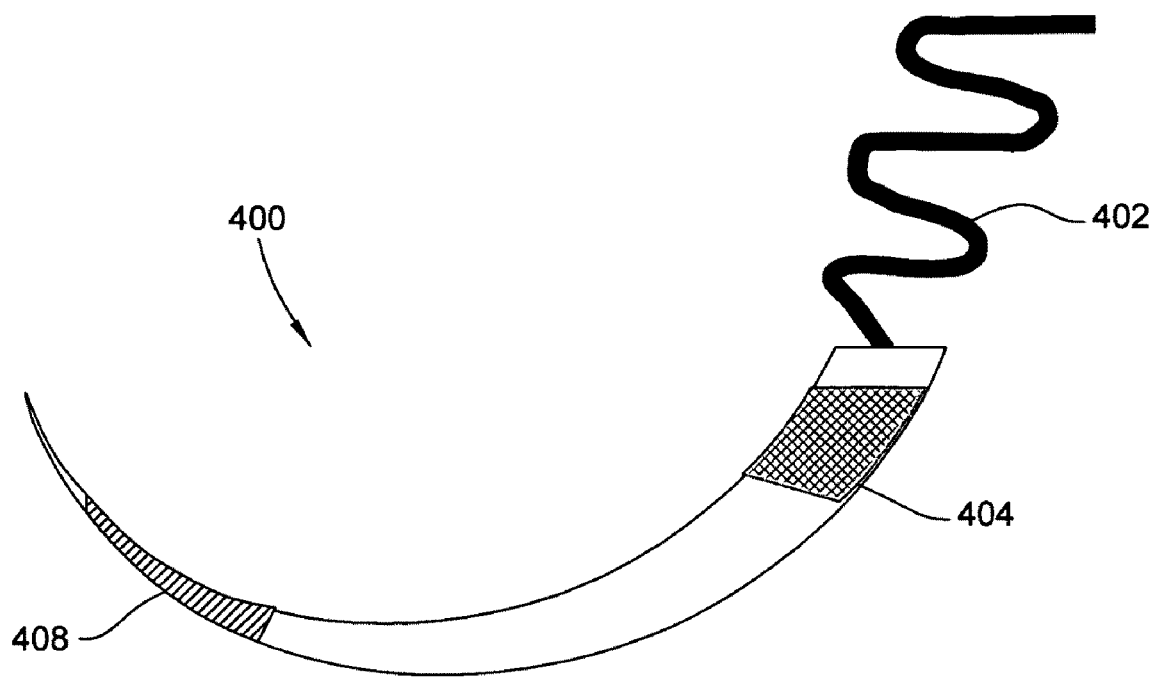
FIG. 8 illustrates a suture needle having two distinct regions that can be detected and distinguished from one another by the system.

For illustrative purposes, consider FIG. 8, which depicts a typical suture needle 400 used for the suturing or "sewing" of tissue. The proximal end of the needle 400, to which is attached the suture thread 402, contains a first region 404 that is marked with a first distinctive pattern and/or color(s). Similarly, the distal end of the needle 400 contains a second region 408 that is marked with a second distinctive pattern and/or color(s). Each of the first and second regions, 404 and 408 respectively, can be detected by the auto-zoom system 10 by means of image analysis algorithms. Consequently, auto-zoom system 10 can distinguish the proximal end of the needle 400 from the distal end of the needle 400, and as a result, can perform different magnification or zoom functions depending on the state of the needle.

Figure 9A:
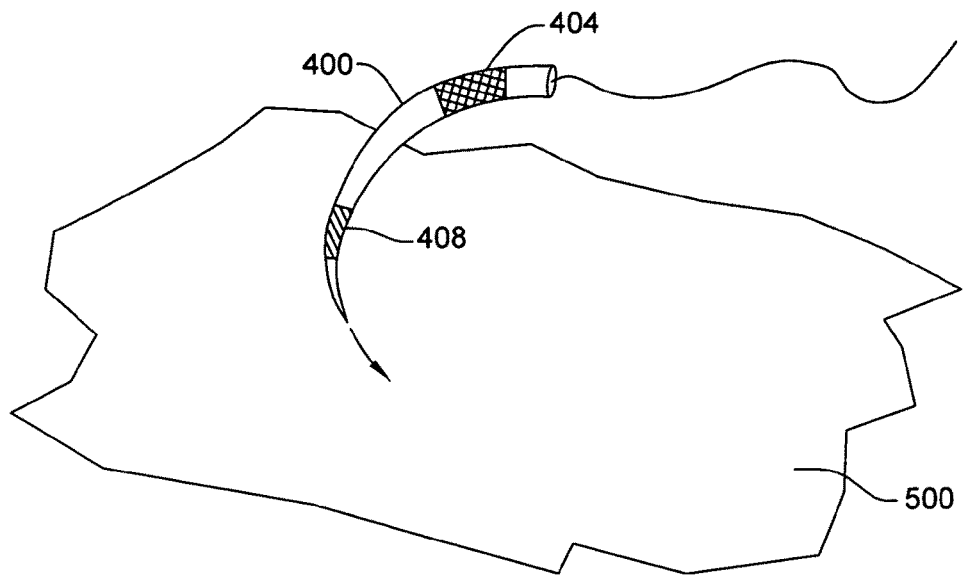
FIGS. 9A-9C illustrate one exemplary embodiment where the suture needle of FIG. 8 can be detected by the system as being in one of three different states.
Figure 9B:
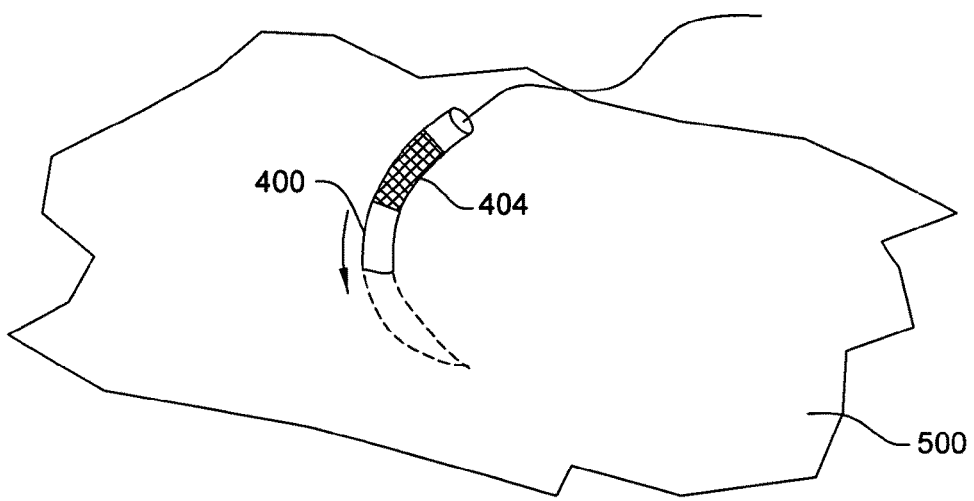
Figure 9C:
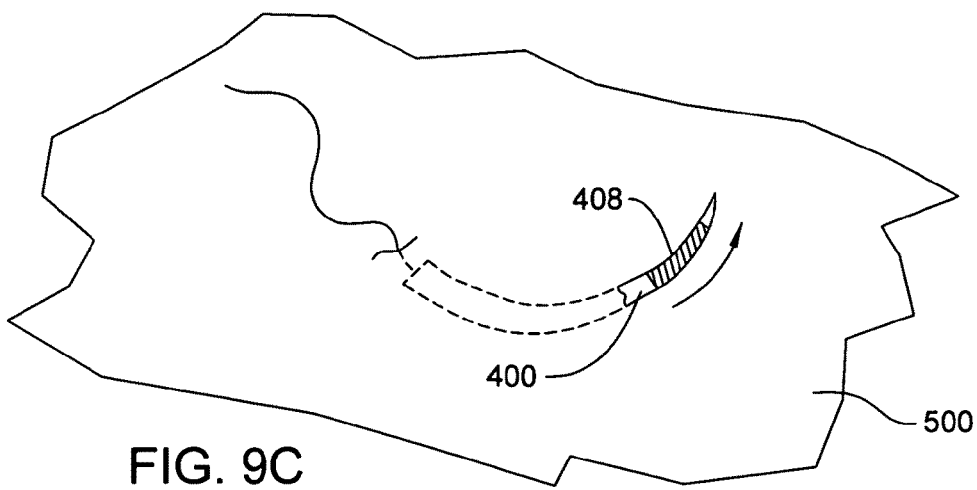

FIGS. 9A-9C illustrate one example of the above embodiment. As depicted in FIG. 9A, suture needle 400 is being directed toward a region of tissue 500 that is to be sutured. When the needle 400 is in this first state, both distinctive regions 404 and 408 are visible and can be detected by system 10. As depicted in FIG. 9B, needle 400 has now penetrated the tissue 500. When in this second state, the distal end of the needle 400, and associated region 408, are no longer visible as they are buried within the tissue 500. Distinct region 404 located at the proximal end of the needle 400 continues to be visible. As depicted in FIG. 9C, needle 400 has now completely penetrated the tissue 500, with the distal end of the needle 400 now protruding out from the tissue 500. When in this third state, the first distinctive region 404 at the proximal end of the needle is no longer visible, while the second distinctive region 408 at the distal end of the needle 400 is once again visible and able to be detected.

As illustrated in FIGS. 9A-9C, the suture needle 400 depicted in the above example exhibits 3 specific states depending on the position of the needle 400 relative to the tissue 500, with either one or both distinctive regions 404 and 408 being visible depending on the state. In the first state, both distinctive regions 404 and 408 are visible and can be detected. In the second state, only the first distinctive region 404 is visible, and thus detectable. In the third state, only the second distinctive region 408 is visible, and thus detectable.

Utilizing these 3 different detectable states, the auto-zoom system 10 can be configured to automatically change the magnification of the endoscope 16 depending on whether the suture needle 400 is completely outside of the tissue 500, in the process of penetrating the tissue 500, or in the process of being removed from the tissue 500. Thus, for example, the system 10 can be configured to automatically adjust the endoscope to operate at a 2× zoom level when the needle 400 is approaching the tissue, automatically switch to a 4× zoom level when the needle begins to penetrate the tissue 500, and then automatically switch back to a 2× zoom level when the needle 400 is being withdrawn from the tissue 500.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A method of automatically controlling a zoom level of a surgical camera, comprising the steps of:
    defining by a user one or more custom zoom parameters associated with one or more surgical instruments;
    capturing a series of images with the surgical camera;
    analyzing the captured images utilizing one or more algorithms to detect the presence of a surgical instrument in the captured images;
    determining one or more default zoom parameters associated with the surgical instrument upon detection of the instrument in the captured images; and
    automatically adjusting the zoom level of the surgical camera based upon the one or more custom zoom parameters associated with the detected surgical instrument if defined by the user, otherwise automatically adjusting the zoom level of the surgical camera based on one or more default zoom parameters associated with the surgical instrument.

2. The method according to claim 1, wherein the step of determining one or more default zoom parameters comprises querying one or more databases of predefined zoom parameters associated with one or more surgical instruments.

3. The method according to claim 1, further comprising the steps of:
    analyzing the captured images to detect at least first and second operating states of the detected surgical instrument;
    determining one or more zoom parameters associated with each detected operating state of the surgical instrument; and
    automatically adjusting the zoom level of the surgical camera for each detected operating state of the surgical instrument.

4. The method according to claim 3, wherein the at least first and second operating states of the surgical instrument are distinguished from one another by detection of at least one region on the surgical instrument that is visually distinctive from other regions of the surgical instrument.

5. The method according to claim 4, wherein the at least one visually distinctive region of the surgical instrument includes at least one of distinctive markings and color.

6. The method according to claim 1, further comprising the steps of automatically adjusting the zoom level of the surgical camera so as to maintain the detected surgical instrument within a field of view of the surgical camera.

7. The method according to claim 1, wherein the step of automatically adjusting the zoom level of the surgical camera comprises the step of automatically adjusting at least one of an optical zoom of the surgical camera and a digital zoom of the surgical camera.

8. The method according to claim 1, further comprising the step of concurrently displaying on at least one monitor first and second images, the first image representing an image captured by the surgical camera at a first zoom level, and the second image representing a portion of the first image being displayed at a second zoom level that is different than said first zoom level.

9. The method according to claim 8, further comprising the step of superimposing one or more graphics upon the first image indicating the portion of the first image that is being displayed in the second image.

10. The method according to claim 1, wherein the surgical camera comprises an endoscopic camera.

11. A method of automatically controlling a zoom level of a surgical camera, comprising the steps of:
capturing a series of images with the surgical camera;
analyzing the captured images utilizing one or more algorithms to detect the presence of a surgical instrument in the captured images;
determining one or more zoom parameters associated with the surgical instrument upon detection of the instrument in the captured images;
automatically adjusting the zoom level of the surgical camera based upon the one or more zoom parameters associated with the detected surgical instrument;
analyzing the captured images utilizing one or more algorithms to detect the presence of a predefined anatomical feature in the captured images;
determining one or more zoom parameters associated with the anatomical feature upon detection of the anatomical feature in the captured images; and
automatically adjusting the zoom level of the surgical camera based upon the one or more zoom parameters associated with the detected anatomical feature,
wherein the captured images are first analyzed to detect the presence of a surgical instrument, and then analyzed to detect the presence of a predefined anatomical feature if no surgical instrument is detected.

12. The method according to claim 11, wherein the surgical camera comprises an endoscopic camera.

13. A method of automatically controlling a zoom level of a surgical camera, comprising the steps of:
capturing a series of images with the surgical camera;
analyzing the captured images utilizing one or more algorithms to detect the presence of a surgical instrument in the captured images;
determining one or more zoom parameters associated with the surgical instrument upon detection of the instrument in the captured images;
automatically adjusting the zoom level of the surgical camera based upon the one or more zoom parameters associated with the detected surgical instrument;
analyzing the captured images utilizing one or more algorithms to detect the presence of a predefined anatomical feature in the captured images;
determining one or more zoom parameters associated with the anatomical feature upon detection of the anatomical feature in the captured images; and
automatically adjusting the zoom level of the surgical camera based upon the one or more zoom parameters associated with the detected anatomical feature,
wherein zoom parameters associated with both a surgical instrument and an anatomical feature are implemented before any zoom parameters associated only with a surgical instrument, which in turn, are implemented before any zoom parameters associated only with an anatomical feature.

14. The method according to claim 13, wherein the surgical camera comprises an endoscopic camera.

15. A method of automatically controlling a zoom level of a surgical camera, comprising the steps of:
automatically configuring the surgical camera to at least primarily utilize digital zoom to view a detected surgical instrument in greater detail when the surgical instrument is detected within a peripheral region of a field of view of the surgical camera;
automatically configuring the surgical camera to at least primarily utilize optical zoom to view the detected surgical instrument in greater detail when the surgical instrument is detected within a central region of the field of view of the surgical camera;
capturing a series of images with the surgical camera;
analyzing the captured images utilizing one or more algorithms to detect the presence of a surgical instrument in the captured images;
determining one or more zoom parameters associated with the surgical instrument upon detection of the instrument in the captured images; and
automatically adjusting the zoom level by adjusting at least one of an optical zoom of the surgical camera and a digital zoom of the surgical camera based upon the one or more zoom parameters associated with the detected surgical instrument.

16. The method according to claim 15, wherein the surgical camera comprises an endoscopic camera.

17. A method of automatically controlling a zoom level of a surgical camera, comprising the steps of:
capturing a series of images with the surgical camera;
analyzing the captured images utilizing one or more algorithms to detect the presence of a predefined anatomical feature in the captured images;
determining one or more zoom parameters associated with the anatomical feature upon detection of the anatomical feature in the captured images; and
automatically adjusting the zoom level of the surgical camera based upon the one or more zoom parameters associated with the detected anatomical feature,
wherein the captured images are first analyzed to detect the presence of a predefined anatomical feature, and then analyzed to detect the presence of a surgical instrument if no predefined anatomical feature is detected.

18. The method according to claim 17, wherein the surgical camera comprises an endoscopic camera.

19. A method of automatically controlling a zoom level of a surgical camera, comprising the steps of:
automatically configuring the surgical camera to at least primarily utilize digital zooming to view a detected anatomical feature in greater detail when the anatomical feature is detected within a peripheral region of a field of view of the surgical camera;

automatically configuring the surgical camera to at least primarily utilize optical zooming to view the detected anatomical feature in greater detail when the anatomical feature is detected within a central region of the field of view of the surgical camera;

capturing a series of images with the surgical camera;

analyzing the captured images utilizing one or more algorithms to detect the presence of a predefined anatomical feature in the captured images;

determining one or more zoom parameters associated with the anatomical feature upon detection of the anatomical feature in the captured images; and automatically adjusting the zoom level of the surgical camera based upon the one or more zoom parameters associated with the detected anatomical feature.

20. The method according to claim 19, wherein the surgical camera comprises an endoscopic camera.

* * * * *